United States Patent [19]
Liotta et al.

[11] Patent Number: 5,990,341
[45] Date of Patent: Nov. 23, 1999

[54] DIASTEREOSELECTIVE SYNTHESIS HYDROXYETHYLENE DIPEPTIDE ISOSTERES

[75] Inventors: Dennis C. Liotta, McDonough; Bharat Ramkrishna Lagu, Atlanta, both of Ga.

[73] Assignee: Emory University, Atlanta, Ga.

[21] Appl. No.: 08/773,684

[22] Filed: Dec. 24, 1996

Related U.S. Application Data

[62] Division of application No. 08/148,990, Nov. 8, 1993, Pat. No. 5,587,514.

[51] Int. Cl.$^6$ ........................ C07C 219/22; C07C 219/06
[52] U.S. Cl. ........................ 560/39; 260/998.2; 530/331; 549/321; 560/29; 560/40; 560/43; 560/45; 560/125; 560/170; 562/444; 562/445; 562/507; 562/567; 564/134; 564/165; 564/191; 564/197
[58] Field of Search ........................ 260/998.2; 530/331; 549/321; 560/29, 39, 40, 43, 45, 125, 170; 562/444, 445, 507, 567; 564/134, 165, 191, 197, 198

[56] References Cited

U.S. PATENT DOCUMENTS

| | | | |
|---|---|---|---|
| 4,329,473 | 5/1982 | Almquist et al. | 546/281 |
| 4,613,676 | 9/1986 | Fuhrer et al. | 560/39 |
| 4,705,846 | 11/1987 | Thaisrivongs | 530/332 |
| 4,758,584 | 7/1988 | Buhlmayer et al. | 514/400 |
| 4,863,905 | 9/1989 | Hudspeth et al. | 514/18 |
| 4,864,017 | 9/1989 | Thaisrivongs | 530/329 |
| 4,880,781 | 11/1989 | Hester, Jr. et al. | 514/18 |
| 4,882,420 | 11/1989 | Thaisrivongs | 530/330 |
| 4,894,437 | 1/1990 | TenBrink | 530/328 |
| 5,091,425 | 2/1992 | Bradury et al. | 514/228.5 |
| 5,120,718 | 6/1992 | Goldman et al. | 514/32 |
| 5,132,400 | 7/1992 | Gammill et al. | 530/317 |
| 5,169,952 | 12/1992 | Askin et al. | 544/137 |
| 5,175,298 | 12/1992 | Wuts | 548/230 |
| 5,187,074 | 2/1993 | Treiber et al. | 435/41 |
| 5,188,950 | 2/1993 | Balani et al. | 435/120 |
| 5,192,668 | 3/1993 | Treiber et al. | 435/41 |
| 5,229,518 | 7/1993 | Plata et al. | 546/243 |
| 5,244,910 | 9/1993 | Baker et al. | 514/326 |

FOREIGN PATENT DOCUMENTS

| | | |
|---|---|---|
| 0 045 161 | 2/1982 | European Pat. Off. |
| 92/21647 | 12/1992 | WIPO |
| WO93/23379 | 11/1993 | WIPO |

OTHER PUBLICATIONS

Bradbury, R.H., et al., "An Efficient Synthesis of the $_\gamma$–Lactone Corresponding to a Hydroethylene Dipeptide Isostere Using Steroselective Bromolactonisation of a Chiral Acyloxazolidinone," *Tetrahedron Letters*, 30:29, pp. 3845–3848 (1989).

Chakravarty, P.K.., et al., "The Synthesis of (2S,4S,5S)–5–(N–Boc)–Amino–6–Cyclohexyl–4–Hydroxy–2–Isopropyl–Hexanoic Acid Lactone, and Hydroxyethylene Dipeptide Isostere Precursor," *Tetrahedron Letters*, 30:4, pp. 415–418 (1989).

Compagnone, R.S. & Rapoport, H., "Chirospecific Synthesis of (+)– Pilocarpine," *J. Org. Chem.*, 51, pp. 1713–1719 (1986).

Decamp, A.E., et al., "Stereocontrolled Addition of Proplonate Homoenolate Equivalents to Chiral –Amino Aldehydes," *Tetrehedron Letters*, 32:16, pp. 1867–1870 (1991).

Diederich, A.M., et al, "Stereoselective Synthesis of a Hydroxyethylene Dipeptide Isostere," *Tetrehedron Letters*, 34:39, pp. 6169–6172 (1993).

Evans, B.E., et al., "A Stereocontrolled Synthesis of Hydroxyethylene Dipeptide Isosteres Using Novel, Chiral Aminoalkyl Epoxides; New Renin Inhibitor Analogs," *Peptides Structure and Function*, Proceedings of the Ninth American Peptide Symposium (1985).

Evans, B.F., et al., "A Stereocontrolled Synthesis of Hydroxyethylene Dipeptide Isosteres Using Novel, Chiral Aminoalkyl Epoxides and γ–(Aminoalkyl) γ–Lactones," *J. Org. Chem.*, 50, pp. 4615–4625 (1985).

Fray, A.H., et al., A Short, "Stereoselective Synthesis of the Lactone Precursor to 2R,4S,5S Hydroxyethylene Dipeptide Isosteres," *J. Org. Chem.*, vol. 51, p. 4826 (1986).

Ghosh, A.K., et al., "An Efficient Synthesis of Hydroxyethylene Dipepetide Isosteres: The Core Unit of Potent HIV–1 Protease Inhibitors," *J. Org. Chem.*, vol. 56, p. 6500 (1991).

Herold, P., et al., "A Versatile and Sterocontrolled Synthesis of Hydroxyethylene Dipeptide Isosteres," *J. Org. Chem.*, 50, pp. 1178–1185 (1989).

Hoffman, R.V., et al., "A Simple Synthetic Approach to Cbz–Phe–$\psi$–(Ch$_2$) Gly–Pro–OMe and Related Peptide Isosteres," *Tetrahedron Letters*, vol. 33:25, pp. 3579–3582 (1992).

Holladay, M.W., et al., "Synthesis of Hydroxethylene and Ketomethylene Dipeptide Isosteres," *Tetrahedron Letters*, 24:41, pp. 4401–4404 (1983).

Hormuth, S. et al., "Titanated Methoxyallene as Novel Homoaldol Equivalent for Diastereoselective Additions to Chiarly Amino Aldehydes," *Angew. Chem. Int. Ed. Engl.*, 32:10, pp. 1449–1450 (1993).

Kano, S., et al., "Stereocontrolled Covergent Synthesis of Hydroethylene Dipeptide Isosteres by the Reaction of –Amino Alehyde with Alkoxytitanium Homenolates," *Teterdedron Letters*, 32:2, pp. 233–236 (1991).

Meek, T.D., "Inhibitors of HIV–1 Protease," *J. Enzyme Inhibition*, vol. 6, pp. 65–98 (1992).

(List continued on next page.)

*Primary Examiner*—Peter O'Sullivan
*Attorney, Agent, or Firm*—Sherry M. Knowles; Jacqueline Haley; King & Spalding

[57] ABSTRACT

A process for the synthesis of hydroxyethylene dipeptide isosteres from α-N,N-di(protected)amino(alkyl or substituted alkyl) methyl ketones that can be efficiently carried out on an industrial scale. The process proceeds with excellent diastereoselectivity and chemical efficiency, and can be used to prepare a wide variety of hydroxyethylene dipeptide isosteres for a variety of uses, including as HIV-1 protease inhibitors and renin inhibitors.

2 Claims, 3 Drawing Sheets

OTHER PUBLICATIONS

Nishi, T. et al., "Diasterselective Synthesis of the Hydroxyethylene Dipeptide Isostere of Leu–Val," *Chemistry Letters*, pp. 1993–1996 (1989).

Sakurai, M., et al., "A New Synthetic Route for the γ–Lactone Precursors of Hydroxyethylene Dipeptide Isosteres," *Tetrahedron Letters*, vol. 34, pp. 5939–5942 (1993).

Szelke, M., et al., "Novel Transition —State Analogue Inhibitors of Renin," Proc. Am. Pept. Symp. 8th, pp. 579–583 (1983).

Vara Prasad, J.N.V., et al., "Addition of Allylic Metals to –Aminoaldehydes. Application to the Synthesis of Statine, Ketomethylene and Hydroxyethylene Dipeptide Isostreres," *Tetrahedron Letters*, vol. 31:13, pp. 1803–1806 (1990).

DIASTEREOSELECTIVE SYNTHESIS HYDROXYETHYLENE DIPEPTIDE ISOSTERES

This application is a divisional of U.S. Ser. No. 08/148,990 filed on Nov. 8, 1993, by Dennis C. Liotta and Bharat Ramkrishna Lagu entitled "Diastereoselective Synthesis of Hydroxyethylene Dipeptide Isosteres," now U.S. Pat. No. 5,587,514.

The U.S. government has rights in this invention by virtue of the partial funding of work leading to this invention through the National Institutes of Health.

This invention is in the area of organic synthesis, and is in particular a diastereoselective synthesis of hydroxyethylene dipeptide isosteres.

BACKGROUND OF THE INVENTION

Hydroxyethylene dipeptide isosteres ("peptide mimics" or "peptidomimetics," illustrated below) are compounds in which a peptide bond is replaced with a non-hydrolyzable hydroxyethyl isostere that mimics a peptide enzymic transition state. Compounds incorporating hdyroxyethyl isosteres have recently generated considerable interest due to their ability to act as HIV-protease and renin inhibitors. Szelke, M., Jones, D. M., Hallet, A., Leckie, B. J., *Proc. Am. Pept. Symp.* 8th, 1983, 579; Meek, T. D., *J. Enz. Inhib.*, 1992, 6, 65. The amino alcohol functionality in active peptidomimetics has (4S,5S) stereochemistry, as indicated below. Peptidomimetics also possess a substituent at the C2 position with the indicated absolute configuration. The "S" or "R" designation of the C2-substituent is a function of substituent priority.

Large quantities of hydroxyethylene dipeptide HIV-protease inhibitors and renin inhibitors are currently in demand for laboratory and clinical testing as well as for potential commercialization. Many of the prior synthetic approaches to these isosteres employ the lactone 1 as a key intermediate which is derivatized via diastereoselective alkylation of the enolate followed by ring opening. Several groups have synthesized 1 from α-amino aldehydes in a variety of ways, including by: (a) addition of a homoenolate equivalent (DeCamp, A. E., Kawaguchi, A. T., Volante, R. P., Shinkai, I., *Tetrahedron Lett.*, 1991, 32, 1867); (b) addition of lithium ethyl propiolate (Fray, A. H., Kaye, R. L., Kleinman, E. F., *J. Org. Chem.*, 1986, 51, 4828); (c) addition of allylic organometallic reagents (Vara Prasad, J. N. V., Rich, D. H., *Tetrahedron Lett.*, 1990, 31, 1803); or (d) by conversion of α-amino aldehydes into α-amino epoxides (Evans, B. E., Rittle, K. E., Homnick, C. F., Springer, J. P., Hirshfield, J., Veber, D. F., *J. Org. Chem.*, 1985, 50, 4615). The synthesis of 1 from a carbohydrate precursor such as D-mannose (Ghosh, A. K., McKee, S. P., Thompson, W. T., *T. Org. Chem.*, 1991, 56, 6500), or via a γ-ketoester derived from N-Cbz-L-phenylalanine (Hoffman, R. V., Kim, H., *Tetrahedron Lett.*, 1992, 33, 3579), N-benzyl-N-BOC-phenylalanine (Dondoni, A., et al., *Tetrahedron Lett.*, 1992, 33, 7259), or N-phthalimido-phenylalanine (Sakurai, M., et al., *Tetrahedron Lett.*, 1993, 34, 5939), have also been reported.

U.S. Patents which disclose methods for the synthesis of hydroxyethylene dipeptide isosteres include U.S. Pat. No. 5,192,668 entitled "Synthesis of Protease Inhibitor," issued Mar. 9, 1993; U.S. Pat. No. 5,188,950 entitled "Method of Preparing HIV Protease Inhibitors," issued Feb. 23, 1993; U.S. Pat. No. 5,187,074 entitled "Method of Hydroxylation with ATCC 55086, " issued Feb. 16, 1993; U.S. Pat. No. 5,175,298 entitled "Dipeptide Hydroxy Ethylene Isostere Synthesis and Intermediate Therefor," issued Dec. 29, 1992; and U.S. Pat. No. 5,169,952 entitled "Stereoselective Production of Hydroxyamide Compounds from Chiral Alpha-Amino Epoxides," issued Dec. 8, 1992.

While these syntheses are successful in producing the target compound, the syntheses proceed with variable stereocontrol, and can exhibit one or more other drawbacks such as a relatively long synthetic sequence, the use of expensive starting materials, or the use of a starting material such as an α-amino aldehyde which is prone to racemization or which produces variable diastereoselectivity depending on the nature of the 'R" group. For example, the Hoffman process (wherein the hydroxyethylene dipeptide isostere is prepared by the alkylation of a t-butyl β-ketoester with an α-bromocarboxylic acid), after hydrolysis, decarboxylation and reduction results in a mixture of 4R and 4S isomers in an approximate ratio of 1.8:1, which must be separated. The DeCamp, et al. process uses an α-amino aldehyde as a starting material that is easily racemized under a variety of experimental conditions. The amino aldehyde is reacted with a titanium homoenolate prepared from ethyl 3-bromopropionate to provide a mixture of (4S/4R) diastereomers that must be separated. The reaction of N,N-dibenzyl-phenylalanine with a dichloroisopropoxytitanium homoenolate using the DeCamp protocol results in a ratio of 4R to 4S diastereomers of greater than 20 to.

Another stereoselective synthesis of hydroxyethylene dipeptide isosteres was recently reported by Diederich and Ryckman. Diederich, "Stereoselective Synthesis of a Hydroxyethylene Dipeptide Isostere," *Tetrahedron Lett.*, 1993, 34, 6169–6172. The Diederich synthesis is based on the conversion of a dibenzyl-L-amino acid to the corresponding N'-methyl-O-methylcarboxamide, which is reacted with a Grignard reagent derived from 2-(2-bromoethyl)-1,3-dioxolane or 2-(2-bromoethyl)-1,3-dioxane to produce a (2S)-2-dibenzylamino-5-[1,3]dioxolan-2-yl-1-phenyl-pentan-3-one or (2S)-2-dibenzylamino-5-[1,3]dioxan-2-yl-phenyl-pentan-3-one, respectively. Reduction of the carbonyl moieties provides the desired amino alcohol function with high 4S-stereoselectivity. The C2-substituent is added by conversion of (2S)-2-dibenzylamino-5-[1,3]dioxolan-2-yl-1-phenyl-pentan-3-one or (2s)-2-dibenzylamino-5-[1,3]dioxan-2-yl-phenyl-pentan-3-one to its corresponding lactone, followed by alkylation of the lactone and ring opening. Diederich's synthesis suffers from the disadvantages that not all of the reagents are commercially available (the Grignard reagents have to be generated), the reagents can be relatively expensive, and the oxidation step requires chromium, which presents waste disposal problems.

None of the known syntheses for hydroxyethylene dipeptide isosteres provides the optimal combination of the use of stable and inexpensive starting materials, high stereoselectivity, high yield, and minimal number of process steps. In light of the strong need for large quantities of hydroxyethylene dipeptide isosteres for the research and development of HIV-protease inhibitors and renin inhibitors, it would be of benefit to provide an economical method for their synthesis.

Therefore, it is an object of the present invention to provide a method for the preparation of hydroxyethylene dipeptide isosteres that results in a product with (4S,5S) stereochemistry.

It is another object of the present invention to provide a method for the preparation of hydroxyethylene dipeptide isosteres that places a substituent group in the C2-position with the proper configuration.

It is another object of the present invention to provide a method for the preparation of hydroxyethylene dipeptide isosteres that is simple and efficient.

It is another object of the present invention to provide a method for the preparation of hydroxyethylene dipeptide isosteres that can be carried out on a manufacturing scale.

SUMMARY OF THE INVENTION

A process is provided for the diastereoselective synthesis of hydroxyethylene dipeptide isosteres from α-N,N-di(protected)amino(alkyl or substituted alkyl) methyl ketones that can be efficiently carried out on an industrial scale. This process is a significant advance over prior known processes for the preparation of this family of compounds, in that the process involves only a small number of steps, the starting material, α-N,N-di(protected)amino(alkyl or substituted alkyl) methyl ketone is less prone to racemization than the prior used aldehydes, and the overall sequence provides excellent diastereoselectivity and chemical efficiency.

Figure 1:
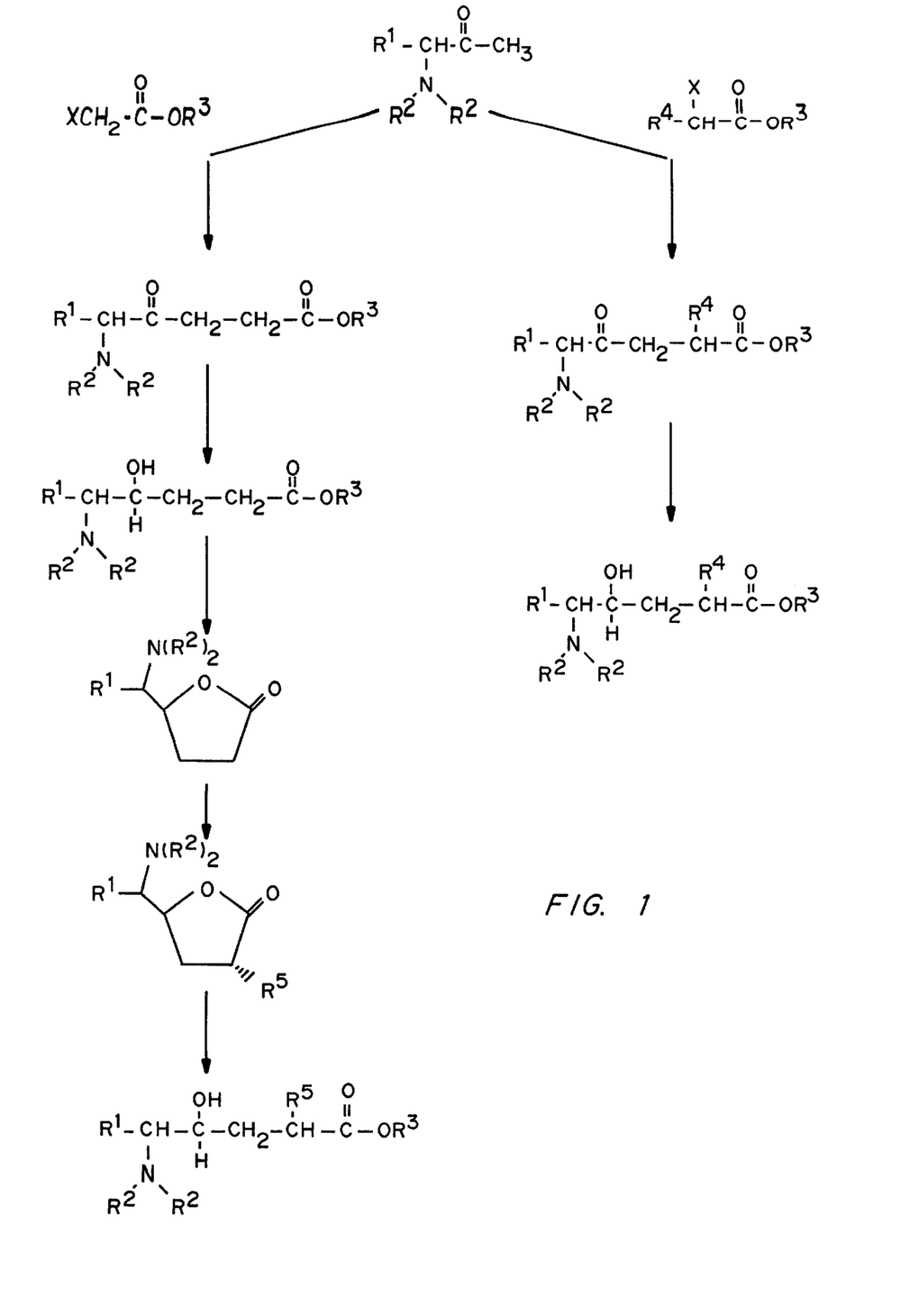
FIG. 1 is a schematic illustration of a method for preparing a hydroxyethylene dipeptide isostere from α-N,N-di(protected)amino(alkyl or substituted alkyl) methyl ketone and an α-(leaving group)-acetate according to the present invention.
Figure 2:
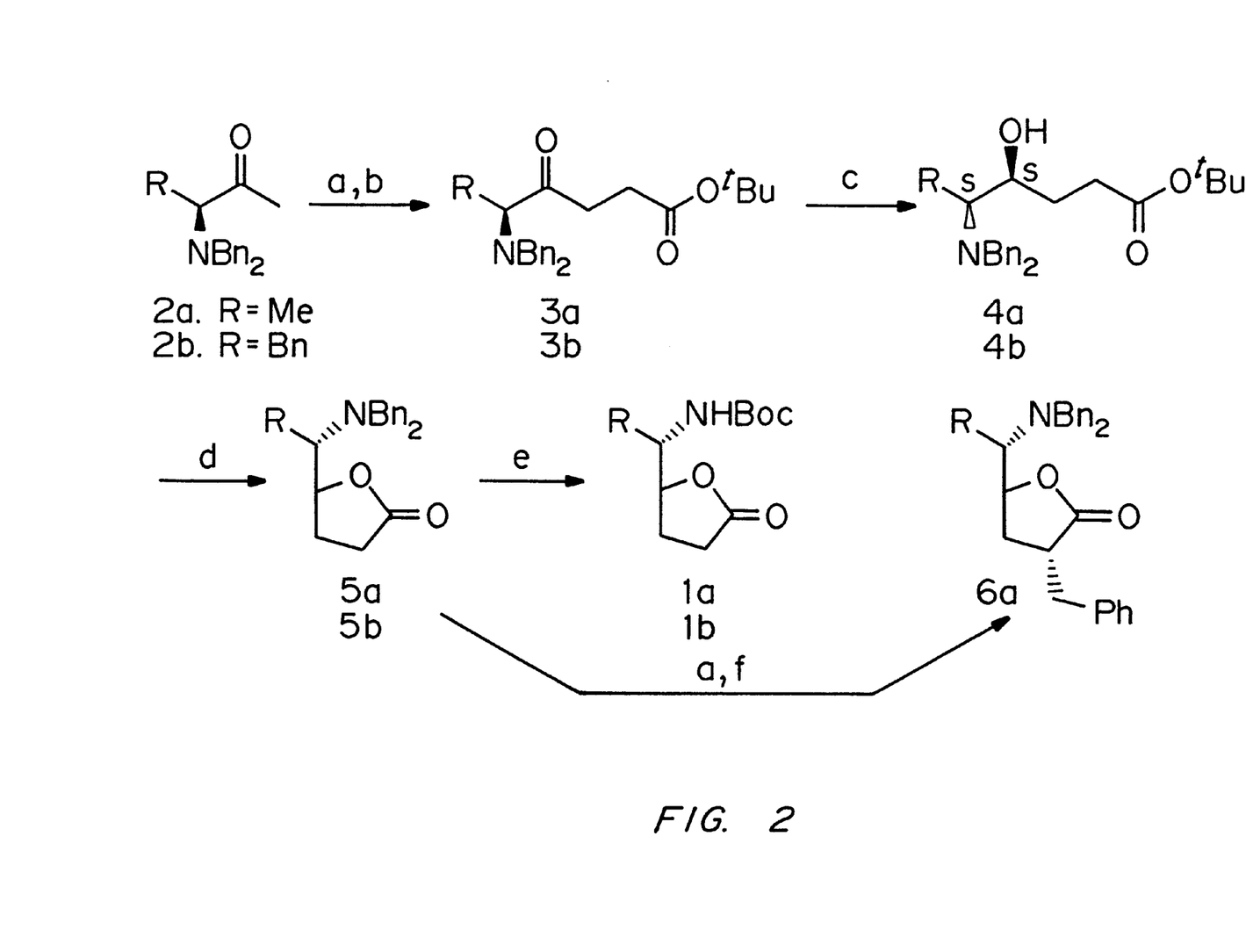
FIG. 2 is a schematic illustration of one method for preparing a peptidomimetic with an alanine or phenylalanine amino-terminus using the following reagents and conditions: a) NaHMDS, THF, $-78°$ C., b) $BrCH_2CO_2t$-Bu, $-78°$ C., c) $NaBH_4$, methanol, $0°$ C., d) toluene, acetic acid, reflux, e) $H_2$/Pd black, absolute ethanol, $BOC_2O$, f) phenyl$CH_2Br$, $-78°$ C., 30 minutes.

The starting α-N,N-di(protected)amino(alkyl or substituted alkyl)methyl ketones can be synthesized according to known procedures. As shown in FIGS. 1 and 2, the ketones are converted into their corresponding γ-keto esters or amides in high yield by treatment with an enolate forming reagent, followed by addition of an α-(leaving group)-acetate or α-(leaving group)-acetamide. The γ-keto ester or amide is then reduced to provide a hydroxyethylene dipeptide precursor with the necessary (4S,5S) stereochemistry.

The important C2-substituent of the hydroxyethylene dipeptide is added by cyclization of the C2-unsubstituted hydroxyethylene dipeptide to its corresponding lactone which is alkylated via its enolate. The lactone is then opened to either a carboxylic acid or amide in good yield. The ester can be converted to the amide according to known procedures.

Figure 3:
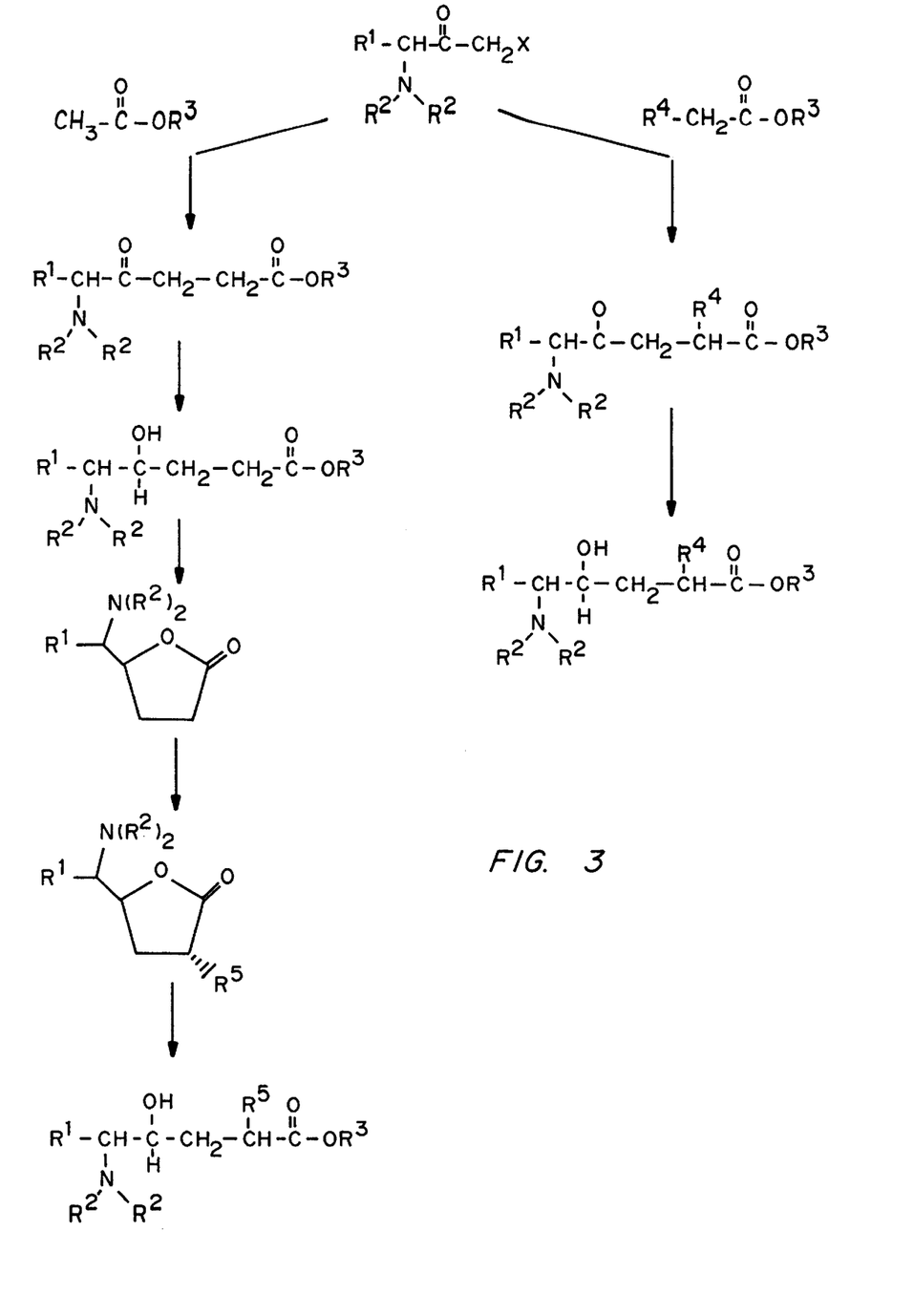
FIG. 3 is a schematic illustration of a method for preparing a hydroxyethylene dipeptide isostere from the enolate of an acetic acid ester and an α-N,N-di(protected)amino(alkyl or substituted alkyl) methyl(leaving group) ketone according to the present invention.

In an alternative embodiment, as shown in FIG. 3, the enolate of an acetic acid ester, amide or the equivalent, is reacted with an α-N,N-di(protected)amino(alkyl or substituted alkyl) methyl(leaving group)ketone to produce the corresponding γ-keto ester, which is treated as described above to produce the peptidomimetic.

In yet another embodiment, illustrated in FIGS. 1 and 3, the C2-substituent is positioned on the starting acetic acid ester or amide.

Using this method, a wide variety of hydroxyethylene dipeptide isosteres can be prepared for a variety of uses, including as HIV-1 protease inhibitors and renin inhibitors.

DETAILED DESCRIPTION OF THE INVENTION

The term alkyl, as used herein, unless otherwise specified, refers to a saturated straight, branched, or cyclic, primary, secondary, or tertiary hydrocarbon of $C_1$ to $C_{10}$, and specifically includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term alkylamino or arylamino refers to an amino group that has one or two alkyl or aryl substituents, respectively.

The term "protected" as used herein and unless otherwise defined refers to a group that is added to an oxygen or nitrogen atom to prevent its further reaction during the course of derivatization of other moieties in the molecule in which the oxygen or nitrogen is located. A wide variety of oxygen and nitrogen protecting groups are known to those skilled in the art of organic synthesis.

The term amino acid as used herein, refers to a natural or synthetic amino acid, and includes, but is not limited to alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaoyl, lysinyl, argininyl, and histidinyl.

The term aryl, as used herein, and unless otherwise specified, refers to phenyl, biphenyl, or naphthyl, and preferably phenyl. The aryl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term halo, as used herein, includes chloro, bromo, iodo, and fluoro.

The term heteroaryl or heteroaromatic, as used herein, refers to an aromatic moiety that includes at least one sulfur, oxygen, or nitrogen in the aromatic ring. Nonlimiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbozolyl, oxazolyl, thiazolyl, isothiazolyl, 1,2,4-thiadiazolyl, isooxazolyl, pyrrolyl, quinazolinyl, pyridazinyl, pyrazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, $N^6$-alkylpurines, $N^6$-acylpurines (wherein acyl is C(O)(alkyl, aryl, alkaryl, or aralkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrimidine, uracil, $N^5$-alkylpyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, and $N^6$-thioalkyl purine, and isoxazolyl. Functional oxygen and nitrogen groups on the heterocyclic base can be protected as necessary or desired during the reaction sequence. Suitable protecting groups are well known to those skilled in the art, and include trimethylsilyl, dimethylhexylsilyl, t-butyldimethylsilyl, and t-butyldiphenylsilyl, trityl, alkyl groups, acyl groups such as acetyl and propionyl, methylsulfonyl, and p-toluylsulfonyl.

The term alkylheterocyclic or alkylheteroaromatic refers to a moiety in which the alkyl group is covalently attached to the heteroaromatic, is preferably $C_1$ to $C_4$ alkylheteroaromatic, and more preferably $CH_2$-heteroaromatic.

The term alkaryl, as used herein, refers to an alkyl group with an aryl substituent, for example, benzyl, α-methyl benzyl, and phenethyl.

The term aralkyl, as used herein, refers to an aryl group with an alkyl substituent.

The term alkoxy, as used herein, and unless otherwise specified, refers to a moiety of the structure —O-alkyl.

The term BOC, as used herein, refers to t-butyloxycarboxy.

The term leaving group, as used herein, refers to a moiety that can be displaced by an enolate or other nucleophile in an $S_N2$ reaction.

The term peptide, as used herein, refers to two or more amino acids connected via amide linkages.

A process is presented for the preparation of hydroxyethylene dipeptide isosteres in which a peptide bond is replaced with a non-hydrolyzable hydroxyethylene isostere, that mimics a peptide enzymic transition state. The process, or standard modifications or extensions thereof, can be used to prepare a wide variety of HIV-1 protease inhibitors and renin inhibitors, including those described in Meek, "Inhibitors of HIV-1 Protease, *Enzyme Inhibition*, 1992, Vol 6., 65–98, incorporated herein by reference.

I. Starting Materials and Intermediates of the Process

In one embodiment, the process, as illustrated in FIG. 1, includes reacting an enolate of an α-N,N-(diprotected) amino ketone of the formula $R^1CHN(R^2)_2C(O)CH_3$ with an α-substituted carboxylic acid ester of the formula $CH_2XC(O)OR^3$ or $R^4CHXC(O)OR^3$, to form a 5-substituted-(5S)-5-(N,N-diprotected amino)-4-oxo-pentanoic acid ester of the formula $R^1CHN(R^2)_2C(O)CH_2CH_2C(O)OR^3$ or $R^1CHN(R^2)_2C(O)CH_2CHR^4C(O)OR^3$, respectively. The latter compound, $R^1CHN(R^2)_2C(O)CH_2CHR^4C(O)OR^3$, on deprotection and reduction of the ketone, provides a selected peptidomimetic with the appropriate (S)-stereochemistry at the 4 and 5 positions, and the $R^4$ substituent in the C2-position. The former compound, $R^1CHN(R^2)_2C(O)CH_2CH_2C(O)OR^3$, can be modified to include a desired substituent (referred to as $R^5$) in the C2-position by reduction of the C4 ketone followed by cyclization to the lactone followed by alkylation via the corresponding enolate, and ring opening. Preferred C2-substituents are benzyl, isobutyl, methyl, isopropyl, cyclohexyl, t-butyl, aryl, and t-alkyl, for example, t-butyl.

When racemic $R^4CHXC(O)OR^3$ is used as a starting material, a diastereomeric product is obtained that can be separated if desired according to known methods. If enantiomerically pure $R^4CHXC(O)OR^3$ is used as a starting material, a single enantiomer is produced.

According to the invention, $R^1$ can be the residue of an amino acid (and preferably a naturally occurring amino acid), i.e., the moiety connected to —$CHNH_2CO_2H$, including but not limited to methyl, ethyl, benzyl, hydrogen, isopropyl, $HOCH_2$—, —$CHOHCH_3$, —$CH_2SH$, 2-methylpropyl, 1-methylpropyl, —$CH_2CH_2SCH_3$, —$CH_2$ (indole), —$CH_2$(p-hydroxyphenyl), $(CH_2)_4NH_2$, —$CH_2$ (imidazole), —$CH_2CH_2C(O)NH_2$, —$CH_2C(O)NH_2$, —$CH_2CO_2H$, —$CH_2CH_2CO_2H$, (wherein functional groups are protected as necessary during the reaction), or other alkyl, aryl, alkaryl, heteroaromatic, alkyl(heteroaromatic), arylamino, or aralkyl group. The $R^1$ moiety should not render the hydrogen on the adjacent carbon acidic and should not contain a carbonyl moiety that would interfere with the reaction. $R^1$ is preferably methyl or benzyl.

$R^2$ is a bulky group that can control the facial selectivity of attack of the enolate on the $CH_2XC(O)OR^3$ or $R^4CHXC(O)OR^3$. $R^2$, which can vary independently on the amine, is preferably a benzyl or substituted benzyl group, wherein the substituent is alkoxy, preferably p-methoxy. In a preferred embodiment, an $R^2$ group is selected that is removed easily from the product of reaction. p-Methoxybenzyl groups can be removed from the amine when desired by oxidation with ceric ammonium nitrate. Tertiary butyl groups can be used to direct the facial selectivity of attack of the enolate, however, they are typically difficult to remove from the product. In a preferred embodiment, the $R^2$ groups on the amine are alike, however, two different $R^2$ groups can be used to protect an amine. For example, the amine can be protected with a combination of benzyl, BOC, benzyloxycarbonyl, or p-methoxybenzyl, however, in a preferred embodiment, at least one of the groups is a benzyl group. An appropriate combination of protecting groups can be selected such that one of the groups can be removed selectively as desired.

$R^3$ can be any moiety that does not adversely affect the $S_N2$ reaction protocol, and in particular, which does not encourage attack by the enolate of the α-N,N-(diprotected) amino ketone on the carbonyl of $CH_2XC(O)OR^3$ or $R^4CHXC(O)OR^3$. Specifically, $R^3$ can be an alkyl, aryl, heteroaromatic, alkylheteroaromatic, aralkyl, alkaryl, and is preferably a bulky group such as t-butyl which hinders addition to the carbonyl by the enolate. It has been noted that when ethyl is the ester moiety using the reaction protocol set out in FIG. 1 using an ethyl-α-bromo-acetate substrate, a complex mixture of products results.

$R^4$ is any group that does not unacceptably slow the rate of, or interfere with the $S_N2$ reaction, for example, a primary, secondary, or tertiary alkyl or alkaryl group, and is most preferably methyl, ethyl, propyl, isopropyl, butyl, isobutyl, cyclohexylmethyl, benzyl or phenethyl. $R^4$ can also be an aryl or aralkyl group, for example, phenyl or alkylphenyl, or a heterocyclic or alkylheterocyclic moiety. In one embodiment, $R^4$ is t-butyl.

X is any moiety that can be displaced in an $S_N2$ reaction, including but not limited to bromo, chloro, iodo, triflate, tosylate, diazonium salts, mesylates, and brosylates.

$R^5$ is any group, which, when attached to X, can be attacked by an enolate ion, resulting in the substitution of the enolate moiety for X, and is typically a primary or secondary alkyl or alkaryl moiety, and is preferably methyl, benzyl, isobutyl, isopropyl, or cyclohexylmethyl.

It is important to note that either $R^4$ or $R^5$ becomes the C2-substituent in the hydroxyethylene dipeptide isostere product. According the process described herein, while $R^5$ is typically limited to primary or secondary alkyl or alkaryl groups because it must be susceptible to attack by an enolate ion in an $S_N2$ reaction, $R^4$ can be a wide variety of moieties, including $R^5$ moieties as well as aryl, heteroaryl and tertiary alkyl groups.

In an alternative embodiment, as shown in FIG. 3, the enolate of an acetic acid ester formed from $CH_3C(O)OR^3$ or $R^4CH_2C(O)OR^3$ is reacted with $R^1CHN(R^2)_2C(O)CH_2X$ to form $R^1CHN(R^2)_2C(O)CH_2CH_2C(O)OR^3$ or $R^1CHN(R^2)_2C(O)CH_2CHR^4C(O)OR^3$, respectively, which is treated as described above to produce the desired peptidomimetic.

In another alternative embodiment, $CH_2XC(O)N(R^6)_2$, $R^4CHXC(O)N(R^6)_2$, $CH_3C(O)N(R^6)_2$ or $R^4CH_2C(O)N(R^6)_2$, wherein $R^6$ is hydrogen, alkyl, alkaryl, aryl, aralkyl, heterocyclic, or alkylheterocyclic, and wherein $R^6$ can vary within the molecule, is used in the reaction sequence in place of the acetic acid ester. For example, a (4S,5S)-hydroxyethylene dipeptide isostere can be prepared by reacting an α-N,N-di(protected)amino methyl(leaving group) ketone with a compound selected from the group consisting of the enolate of acetic acid ester and and the enolate of acetamide to form the corresponding γ-keto ester, which is further derivatized as described in detail herein.

Some of the compound intermediates used in the disclosed process are novel compounds (wherein $R^1$, $R^2$, $R^3$, and $R^4$ are as defined above unless indicated otherwise), including but not limited to:

(i) $R^1CHN(R^2)_2C(O)CH_2CHR^4C(O)OR^3$, wherein $R^4$ is as defined above;

(ii)

wherein $R^4$ is aryl, aralkyl, heteroaryl or t-alkyl;

(iii)

wherein $R_2$ and $R^6$ are independently (and can vary within the molecule) as defined above or hydrogen; and (v) $R^1CHN(H^2)_2C(O)CH_2CHR^4C(O)OH$, wherein $R^4$ is as defined above.

Compounds (i) and (v) can be used as intermediates to prepare compounds that have a second moiety on the carbon alpha to the carbonyl via appropriate enolate reactions using Compounds (ii). Compounds (iii) can be used to prepare Compounds (iv), which can be used in vitro as research tools to study the structure-activity relationship, including bulk tolerance relationships, of HIV-protease inhibitors and renin inhibitors, or which can be used in vivo as HIV-protease inhibitors and renin inhibitors which are administered as disclosed in U.S. Pat. No. 5,244,910 entitled "Renin Inhibitors," issued Sep. 14, 1993; U.S. Pat. No. 4,894,437 entitled "Novel Renin Inhibiting Polypeptide Analogs Containing S-Aryl-D- or L- or DL-cysteinyl, 3-(Arylthio)Lactic Acid or 3-(Arylthio)Alkyl Moieties," issued Jan. 16, 1990; U.S. Pat. No. 4,882,420 entitled "Dihalo-Statine Substituted Renin Inhibitors," issued Nov. 21, 1989; U.S. Pat. No. 4,880,781 entitled "Renin Inhibitory Peptides Containing an N-Alkyl-Histidine Moiety," issued Nov. 14, 1989; U.S. Pat. No. 4,864,017 entitled "Novel Renin Inhibiting Peptides Having a Dihydroxyethylene Isostere Transition State Insert," issued Sep. 5, 1989; and U.S. Pat. No. 4,705,846 entitled "Novel Renin Inhibiting Peptides having a Gamma Lactam Pseudo Dipeptide Insert," issued Nov. 10, 1987.

II. Description of Process Steps

The process steps for preparing hydroxyethylene dipeptide isosteres are described in more detail below. Given this disclosure, one of ordinary skill in the art will be able to routinely modify the synthetic steps as desired or necessary to achieve specific results. Modifications of the process steps or equivalent steps are considered to fall within the scope of this invention.

All of the reactions described below can be carried out in standard organic solvents that do not react or otherwise interfere with the process. Given the description of the process steps below, one of ordinary skill in the art of organic synthesis will be able to select an appropriate solvent for each step. Preferred solvents are typically tetrahydrofuran and acetonitrile. Other solvents that can be considered for selected reactions include a dialkyl formamide, such as dimethyl formamide; dialkyl sulfoxide such as dimethyl sulfoxide; chlorinated solvents such as d-chloromethane, chloroform, carbon tetrachloride, trichloroethane, and tetrachloroethane; alcohols such as methanol, ethanol, and propanol; benzene, alkylated benzenes such as toluene, o, m, and p-xylene; alkoxybenzenes such as o, m, and p-cresol; ethers such as methyl t-butyl ether, tetrahydrofuran, and diethyl ether; glymes such as diglyme and triglyme; straight chain or branched alkyl solvents such as hexane, hexanes, heptane, pentane, and petroleum ether (ligroin); alkyl nitriles other than acetonitrile; nitroalkyl solvents such as nitromethane; and perfluoroalkyl solvents.

Step 1 Preparation of α-N,N-Di(protected)amino(alkyl or substituted alkyl) Methyl Ketone α-N,N-Di(protected)amino(alkyl or substituted alkyl) methyl ketones can be prepared as described in Lagu, et al, "Highly Diastereoselective Aldol Reactions of Chiral Methyl Ketones," *J. Org. Chem.*, 1993, 58, 4191–4193, or Reetz, et al., *Tetrahedron: Asymmetry*, 1992, 1, 375. Generally, a selected amino acid, for example, a naturally occurring amino acid, is first converted to its N,N-diprotected derivative using known procedures. The protecting group typically also adds to the carboxylic acid moiety, forming an ester that can be removed by selective hydrolysis or selective catalytic transfer hydrogenolysis (Bajwa, *Tetrahedron Lett.*, 1992, 33, 2299). The amino-protected carboxylic acid can be converted to the desired ketone using published or otherwise known procedures, for example, the Mukaiyama or Jorgenson-Gilman protocols (Mukaiyama, et al., *Chem. Lett.* 1974, 663; Jorgenson, *J. Org. React.* 1970, 18, 1) Reetz, et al., synthesized α-N,N-dibenzyl amino ketones from the corresponding α-(L)-amino acids. They reported that the nitrogen protecting group on the α-(L)-amino acid has an influence on the diastereoselectivity of nucleophilic addition. Reetz also reported that the keto group can be reduced with excellent diastereoselectively to yield a vicinal amino alcohol with S,S stereochemistry at the stereogenic centers. Reetz, M. T., Drews, M. W., Lennick, K., Schmitz, A., Holdgrun, X, *Tetrahedron: Asymmetry*, 1990, 1, 375; Reetz, M. T., Drews, M. W., Matthews, B. R., Lennick, J., *J. Chem. Soc., Chem. Commun.*, 1989, 1474.

Lagu, et al, has reported that aldol reactions of lithium enolates of α-(N,N-dibenzylamino)alkyl methyl ketones proceed diastereoselectively with a variety of aldehydes. Neither Reetz nor Lagu extended their study to the use of α-(N,N-diprotected)alkyl methyl ketones in $S_N2$ displacement reactions.

Step 2 Generation of the Enolate of α-N,N-Di(protected) amino(alkyl or substituted alkyl) Methyl Ketone (FIG. 1) or the Enolate of Acetic Acid Ester (FIG. 3) and Preparation of γ-keto ester

In the second step according to this process, α-N,N-di (protected)amino(alkyl or substituted alkyl) methyl ketone (FIG. 1) or a selected acetic acid ester or other carboxylic acid ester (FIG. 3) or the corresponding amide is converted to its corresponding enolate, which is reacted with an α-(leaving group) acetic acid ester or α-N,N-di(protected) amino(alkyl or substituted alkyl) methyl(leaving group) ketone, respectively, in an $S_N2$ process to provide a desired γ-keto ester.

It should be noted that α-N,N-di(protected)amino(alkyl or substituted alkyl) methyl ketone can form either a thermodynamic (most highly substituted) enolate or a kinetic (least substituted) enolate. In this process, it is necessary to generate the kinetic enolate of the methyl ketone. In contrast, the acetic acid ester can only form one type of enolate because the carbonyl is flanked by an —OR$^3$ moiety on one side.

Lithium or sodium salts of hindered nitrogen bases are often used to form enolates. A variety of groups can be used to hinder the amine in the hindered nitrogen base, as known to those skilled in the art. Preferred reagents to generate enolates include amide bases such as LDA, sodium hexamethyldisilazide (NaHMDS), and potassium hexamethyldisilazide (KHMDS), optionally in combination with HMPA, TMEDA, or other reagents, as known to those skilled in the art. Sodium hexamethyldisilazide is a preferred reagent for the formation of the enolate of α-N,N-di(protected)amino (alkyl or substituted alkyl) methyl ketone in this process. The sodium enolate produced by sodium hexamethyldisilazide is more ionic, and less regiostable, than its lithium counterpart. The use of lithium enolates also results in slightly lower yields in certain cases.

Other enolate forming reagents that can be used in this process include hydride sources such as KH or NaH alone, or trialkyl silyl hydrides with $Co_2(CO)_8$, titanium enolate forming reagents, for example, $TiCl_4$ and boron enolate forming reagents, for example from $Bu_2BOTf$.

In one embodiment, a enolate is generated in a derivative of the acetic acid ester or amide in which the moiety attached to the carbonyl is a chiral auxiliary, as illustrated below. A wide variety of auxiliaries are known to those skilled in the art, as discussed, for example, in Heathcock, C. H., *Modern Synthetic Methods*; Scheffold, R., Ed.; Verlag Helvetica Chimica Acta: CH-400 Basel, 1992; pages 1–102; d Evans, D. A., *Asymmetric Synthesis*, Vol. 3. Academic Press, New York, 1984, Chapter 1. Chiral auxiliaries can simultaneously control both the enolate geometry and the facial selectivity of its reactions with electrophiles. This provides a means of controlling the stereochemistry at the C2 carbon. Many chiral auxiliaries are imides. Other examples of commonly used auxiliaries are 4-methyl-5-phenyl-2-oxazolidinone; 4-benzyl-2-oxazolidinone; 4-isopropyl-2-oxazalidinone, and 2,10-camphorsultam.

-continued

The enolate is typically generated in situ in an inert solvent such as tetrahydrofuran under an inert atmosphere such as argon or nitrogen. Other suitable solvents include other ethereal solvents such as diethyl ether and hydrocarbon solvents such as pentane and toluene. The α-(leaving group) acetic acid ester or α-N,N-di(protected)-amino(alkyl or substituted alkyl) methyl(leaving group) ketone is added slowly to the reaction solution. This reaction is typically carried out at a temperature ranging between −78 and 0 degrees centigrade, for a time ranging from approximately 30 minutes to two hours, or until completion of reaction.

Step 3 Reduction of γ-Keto Ester to a Hydroxyethylene Dipeptide Isostere

In Step 3, the γ-keto ester prepared in Step 2 is reduced to the corresponding hydroxyethylene dipeptide isostere using known procedures. A preferred reducing agent is sodium borohydride. Other suitable reducing agents include diisobutylaluminum hydride (DIBAL-H), lithium borohydride (LiBH$_4$), and sodium bis(2-methoxyethoxy)-aluminum hydride (Red-Al). The reduction is typically carried out at low temperature, for example, 0 degrees centigrade, for one hour, or until the reduction is complete. The reaction can be conducted in anhydrous methanol or other suitable solvent.

Step 4 Cyclization of Hydroxyethylene Dipeptide Isostere

Active hydroxyethylene dipeptide isosteres have a C2-substituent. Alkyl and alkaryl groups can be added to the C2-position of a C2-unsubstituted hydroxyethylene dipeptide isostere by cyclization of the isostere to the corresponding lactone, followed by alkylation of the lactone through its enolate and ring opening.

Cyclization of the γ-hydroxy carboxylic acid ester can be accomplished under acidic conditions as known to those skilled in the art, including by treatment with methanesulfonic acid and glacial acetic acid in dry toluene. Other acids that can be used in the cyclization process include, but are not limited to, sulfuric acid and resinous sulfonic acids, such as Dowex-50 and Nafion, alkylsulfonic acids other than methanesulfonic acid, arylsulfonic acids, hydrobromic acid, hydrochloric acid, phosphoric acid, alkylphosphoric acid, nitric acid, nitrous acid, carboxylic acids and diacids, for example as acetic acid, formic acid and oxalic acid. The cyclization is typically conducted under anhydrous conditions at 80–111 degrees Centigrade for six to twelve hours, or until the cyclization is complete.

The process embodiment wherein R$^4$CHXC(O)OR$^3$ or R$^4$CH$_2$C(O)OR$^3$ is used as a starting material to form R$^1$CHN(R$^2$)$_2$C(O)CH$_2$CHR$^4$C(O)OR$^3$ obviates the need to carry out Steps 4, 5 and 6, wherein the C2-substituent (R$^5$) is added to the hydroxypeptide isostere via an enolate reaction.

Step 5 Alkylation of Lactone

The lactone prepared as described in Step 4 or as otherwise known in the art is alkylated through its enolate according to known procedures. The enolate can be generated in an inert solvent under an inert atmosphere as described in Step 2. A preferred base for the generation of the enolate is sodium hexamethyldisilazide. The enolate is typically generated under anhydrous conditions at a temperature ranging from approximately −78 to −60 degrees Centigrade. After generation of the enolate, a selected XR$^5$ is added to the reaction solution. The reaction is allowed to proceed to completion, generally in thirty minutes to one hour.

Step 6 Ring Opening of Lactone

The alkylated lactone prepared as described in Step 5 or as otherwise known in the art can then be converted into the required isostere by a ring opening reaction using the Weinreb amidation protocol. Basha, A., Lipton, M., Weinreb, S. M., *Tetrahedron Lett.*, 1977, 4171. Alternatively, the lactone can be opened to the corresponding carboxylic acid, that can be converted to the desired isostere using known procedures.

Examples 1–7 provide a detailed description for one process for the preparation of the peptidomimetic (5S)-5-(N,N-dibenzylamino)-2-ethyl-(4S)-4-hydroxy-hexanamide according to the present invention, illustrated in FIG. 2. This example is merely illustrative, and not intended to limit the scope of the invention.

EXAMPLE 1

Preparation of N,N-dibenzylalanine

Benzaldehyde (7.0 mmol, 7.0 mL) was added to a suspension of L-alanine (20.0 mmol, 1.78 g) in acetonitrile (30.0 mL) and water (20.0 mL) at room temperature. The resulting turbid solution was stirred at room temperature for 30 minutes. Sodium cyanoborohydride (2.5 eq., 50.0 mmol, 3.2 g) was then added in one portion, and the resultant yellowish solution was stirred for 60 minutes (exothermic reaction). A few drops of glacial acetic acid were added in order to maintain a pH of approximately 6. After 30 minutes, a white precipitate appeared. The suspension was filtered through a sintered glass funnel using 100 mL of diethyl ether. The organic solvents were removed in vacuo. The aqueous solution was extracted with Et$_2$O (2×75 mL), and the organic layer was washed with brine. The organic layer was then dried over anhydrous sodium sulfate, filtered, and the solvent was removed in vacuo to yield 13.0 g of yellow liquid. Benzaldehyde and benzyl alcohol were removed by distillation under reduced pressure. The yellow solid was further purified by column chromatography on silica gel with 1:1 hexanes/ethyl acetate as the eluting system (Rf=0.2) to yield 2.8 g (52%) of N,N-dibenzyl alanine. $^1$H NMR (300.15 MHz) δ 1.39 (d, J=7.2 Hz, 3H), 3.54 (q, J=8.7 Hz, 1H), 3.70 (ABq, δ A=3.54, δ 6=3.85, J=16.2 Hz, 4 H), 7.26–3.38 (m, 11 H); HRMS for C$_{17}$H$_{20}$NO$_2$: 270.149. (calc'd 270.1489).

13

EXAMPLE 2

Preparation of α-(N,N-dibenzylamino)ethyl methyl ketone

Triethylamine (8.85 mmol, 1.24 mL) was added under an argon atmosphere to a stirred solution of N,N-dibenzylalanine (8.85 mmol, 2.38 g) in tetrahydrofuran (THF) (53.0 mL) at −30° C. (dry ice/CCl$_4$ bath). Trimethyl acetyl chloride (8.85 mmol, 1.42 mL) was then added dropwise via syringe and the turbid solution was allowed to stir at −30° C. for 30 minutes before dropwise addition of a solution of methylmagnesium chloride in THF (3.0M, 1.07 eq., 9.5 mmol, 3.23 mL) over 10 minutes. The solution was stirred for 45 minutes and then quenched with saturated solution of NH$_4$Cl (5.0 mL). The solution was extracted with Et$_2$O, the organic extracts washed with brine, dried over MgSO$_4$, and filtered. The solvent was evaporated in vacuo and the residue was subjected to flash column chromatography on silica gel with 8:1 hexanes/ethyl acetate to isolate a pure product in 65% yield. Colorless oil; R=0.43 (7:1 hexanes/ethyl acetate) $^1$H NMR (300.15 MHz) δ 1.19 (d, J=5.4 Hz, 3 H), 2.25 (5, 3 H), 3.39 (q, J=6.9 Hz, 1 H), 2.57 (AB quartet, δ$_A$=3.33, δ$_B$=3. JAS=13.8 Hz, 4 H), 7.19–7.43 (m, 10 H); $^{13}$C NMR (75.5 MHz 7.1, 27.7, 54.6, 62.9, 27.2, 128.5, 128.8, 139.3, 210.8; IR (Neat) 1710 cm$^{-1}$; MS (low resolution) m/e 268 M+H 22%), 224 (MeCHNBn$_2$, 100%); HRMS for C$_{18}$H$_{22}$NO: 268–1709 (calc'd 268–1676); Anal: calc'd for C$_{18}$H$_{21}$NO: C 80.68, H 7.92, N 5.24; Found: C 80.79, H 7.95, N 5.17.

EXAMPLE 3

Preparation of (5)-5-(N,N-dibenzylamino)-4-oxo-hexanoic acid-tert-butyl ester Tetrahydrofuran (5.5 mL) was introduced via syringe to a three-necked 25 mL round bottom flask purged with argon. The flask was cooled to −78° C. with a dry ice-acetone bath, and a solution of sodium hexamethyldisilazide in THF (3.3 eq., 1.0 M, 3.3 mL) was added. Compound 2a (α-(N,N-dibenzylamino)ethyl methyl ketone, 1.0 eq., 3.0 mmol) in THF (3.5 mL) was then added dropwise via syringe. The resultant yellow solution was allowed to stir at −78° C. for 1 hour, after which t-butyl α-bromoacetate (3.1 mmol, 0.48 mL) was added neat to the enolate solution. The reaction was quenched at −78° C. with a saturated solution of NH$_4$Cl after 30 minutes. The solution was extracted with Et$_2$O (2×20 mL), and the organic layer was separated and dried over anhydrous sodium sulfate. The solvent was removed in vacuo and the resultant yellow oil was then purified by flash column chromatography on silica gel with 8:1 hexanes/ethyl acetate as the eluting system to obtain the product in 94% yield. Colorless oil, $^1$H NMR (300–15 MHz) δ 1.22 (d, J=G-C$^1$ 3 H), 1.44 (s, 9 H), 2.40–2.55 (m, 2 H), 2.70–2.81 (m, 1 H), 3.04–3.18 (m, 1 H), 3–45 (q, J=6–9 Hz, 1 H), 3.62 (AB quo δ$_A$=3.49, δ$_B$=3.75, JAB=13.5 Hz, 4 H), 7.25–7.51 (m 10 H); $^{13}$C NMR (75.5 MHz) 7.1, 28.0, 29.4, 34.9, 54.5, 62.2, 80.2, 127.1, 128.4, 128.7, 139.2, 171.9, 210.9; IR (Neat) 1720 cm$^{-1}$(br); MS (low res.) 382.4 (M+1, 21%), 326.3 (M-$^t$Bu, 7%), 224.3 (MeCHNBn$_2$, 100%); HRMS for C$_{24}$H$_{32}$NO$_3$: 282.2373 (calc'd 382.2374); Anal: calc'd for C$_{24}$H$_{31}$NO$_3$: C 75.55, H 8–19, N 3.67, O 12.58; Found: C 75–54, H 8.21, N 3.63.

EXAMPLE 4

Reduction of (5S)-5-(N,N-dibenzylamino)-4-oxo-hexanoic acid-tert-butyl ester (3a) to (5s)-5-(N,N-dibenzylamino)-44-hydroxy-hexanoic acid-tert-butyl ester (4a)

Sodium borohydride (2.0 eq., 3.3 mmol, 0.12 g) was added in one portion with stirring to a solution of (5S)-5-(N,N-dibenzylamino)-4-oxo-hexanoic acid-tert-butyl ester (1.65 mmol, 0.63 g) in anhydrous methanol (20.0 mL) at 0° C. (ice-water bath). The solution was stirred for two hours and then quenched carefully with water (5.0 mL). Methanol was removed in vacuo and the residue was extracted with Et$_2$O, washed with brine, and dried over anhydrous Na$_2$SO$_4$. The solvent was removed and the colorless viscous oil obtained (crude wt.=0.65 g) was used in the reaction described in Example 5 without further purification. $^1$H NMR (300.15) δ 1.02 (d, J=6.9 Hz, 3 H), 1.29 (s, 9 H), 2.01–2.58 (m, 4 H), 3.54 (AB quartet, δ$_A$=3.29, δ$_B$=3.80, JAB=13.2 Hz, 4 H), 3.41–3.49 (m, 1 H), 4.45 (br, S, 1 H), 7.22–7.35 (m, 10 H); MS (low res.) 384 (m+1, 18%), 328 (M-$^t$Bu, 11%), 224 (MeCHNBn$_2$, 100%); HRMS for C$_{24}$H$_{34}$NO$_3$: 384.2538 (calc'd 384.2530).

EXAMPLE 5

Cyclization of (5S)-5-(N,N-dibenzylamino)-4S-hydroxy-hexanoic acid-tert-butyl ester (4a) to (5S)-5[(1S)-1-(N,N-dibenzylamino)-ethyl]-dihydrofuran-2(3H)-one (5a)

Glacial acetic acid (0.4 mL) and one drop of methanesulfonic acid were added to a solution of (5S)-5-(N,N-dibenzylamino)-4-hydroxy-hexanoic acid-tert-butyl ester (0.6 g, 1.57 mmol) in dry toluene (15.0 mL) in a 50 mL round bottom flask fitted with a reflux condenser. The reaction mixture was heated at reflux for 12 hours and then cooled to ambient temperature. The pH of the solution was adjusted to 7 by slow addition of a saturated solution of NaHCO$_3$. The organic layer was separated, and the aqueous layer was extracted with Et$_2$O (10 mL). The combined organic extracts were dried over MgSO$_4$, filtered, and the solvent was removed in vacuo. The residue thus obtained was purified by flash column chromatography on silica gel with 4:1 hexanes/ethyl acetate to obtain 0.41 g (85% yield) of pure (5S)-5[(1S)-1-(N,N-dibenzylamino)-ethyl]-dihydrofuran-2(3H)-one (5a). White solid, mp. 61–62° C., $^1$H NMR (300.15) δ 1–11 (d, J=6.6 Hz, 3 H), 1.83–2.15 (m, 2 H), 2.44–2.50 (m, 2 2.86 (pentet, J=6.9 Hz, 1 H), 3.71 (ABq, δ$_A$=3.87, δ$_B$=3.56, JAB=13.8 Hz, 4 H), 4.49 (pentet, J=7.2 Hz, 1 H), 7.10–7.41 (m, 10 H); $^{13}$C NMR (75.8 MHz) 10.9, 25.6, 28.7, 54.3, 55.8, 83.1, 126.8, 128.2, 128.7, 139.9, 177.1; MS (10W res.) 310 (M+1, 20%), 224 (MeCHNBn$_2$, 40%), 91 (NBn$_2$, 100%); HRMS for C$_{20}$H$_{24}$NO$_2$: 310.1807 (calc'd 310.1801); Anal calc'd for C$_{20}$H$_{23}$NO$_2$: C 77.64, H 7.49, N 4.53; Found: 77.54, H 7.55, N 4.49.

EXAMPLE 6

Alkylation of (5B)-5[(1S)-1-(N,N-dibenzylamino)-ethyl]-dihydrofuran-2(3H)-one to (3S)-3-benzyl-(5S)-5-[(1S)-1-(N,N-dibenzylamino)-ethyl]-dihydrofuran-2(3H)-one (6a)

To a stirred solution of sodium hexamethyldisilazide (0.27 mmol, 0.27 mL) in 1.0 mL THF at −78° C., a solution of lactone 5a (0.25 mmol, 0.08 g) in THF (0.5 mL) was added via a syringe under argon atmosphere. The solution was stirred at −78° C. for 1 hour and then treated with benzyl bromide (0.27 mmol, 0.3 mL). The reaction mixture was quenched after 30 minutes with saturated solution of NH$_4$Cl. The organic layer was separated and the aqueous layer was extracted with Et$_2$O (10 mL). The combined organic extracts were dried over MgSO$_4$, filtered and the solvent was removed in vacuo. The residue was further purified by column chromatography under standard conditions to give the alkylated lactone (3S)-3-benzyl-(5S)-5-[(1S)-1-(N,N-dibenzylamino)-ethyl]-dihydrofuran-2(3H)-one (6a) in 81% yield (0.8 g). White solid, $^1$H NMR (300.15) δ 1.05 (d, J=6.9 Hz, 3 H), 1.81–2.01 (m, 2 H) 2.74–3.17 (m, 4 H), 3.66 (AGq, δ$_A$=3.50, δ$_B$=3.82, JAB=13.8 Hz, 4 H), 4.25 (q, J=6.6 Hz, 1 H), 7.16–7.38 (m, 15 H); $^{13}$C NMR 11.1, 30.4, 36.6, 41.2, 54.3, 55.6, 81.1, 126.7, 128.2, 128.6=128.9, 138.2, 139.9, 178.7.

EXAMPLE 7

Ring Opening Amidation of (3S)-3-benzyl-(5S)-5-[(1S)-1-(N,N-dibenzylamino)-ethyl]-dihydrofuran-2 (3H)-one (6a).

The amidation can be carried out as described in Basha, A., Lipton, M., Weinreb, S. M., *Tetrahedron Lett.*, 1977, 4171

Examples 8 and 9 provide a detailed description for the preparation of (5S)-5-(N,N-dibenzylamino)-2-ethyl-4-oxo-hexano-(N,N-diethyl)-amide.

EXAMPLE 8

Preparation of 2-bromo-(N,N-diethyl)-butyramide

The synthesis of the 2-bromo-(N,N-diethyl)-butyramide can be carried out as described by Compagnone, R. S., and Rapoport, H. *J. Org. Chem.* 1986, 51, 1713. Briefly, to a solution of (±)-2-bromobutyric acid (10.0 mmol, 1.67 g) in THF (20.0 mL) at −10° C. under argon atmosphere was added triethylamine (10.7 mmol, 1.49 mL) followed by isobutyl chloroformate (10.7 mmol, 1.39 mL) dropwise. Diethylamine (12.5 mmol, 1.29 mL) was added to this suspension at −10° C. and the reaction mixture was stirred for 40 minutes. The reaction was quenched by addition of 5.0 mL of a 5% solution of citric acid. The crude product was extracted with Et$_2$O, washed with brine, dried over MgSO$_4$ and solvent evaporated in vacuo to provide 2.4 g of residue which was purified by column chromatography over silica gel with 4:1 hexanes-ethyl acetate as the solvent system (Rf=0.25). The product, 2-bromo-(N,N-diethyl)-butyramide, was obtained in 66% yield (1.46 g) as a colorless liquid. Analytical data: $^1$H NMR (300.15 MHz) δ 0.90 (t, J=7.5 Hz, 3H), 1.05 (t, J=7.2 Hz, 3H), 1.16 (t, J=7.2 Hz, 3H), 1.85–2.21 (m, 2H), 3.08–3.52 (m, 4H), 4.20 (t, J=7.2 Hz, 1H); $^{13}$C NMR (75.5 MHz) 12.1, 12.3, 14.7, 28.3, 40.8, 42.2, 45.5, 167.8; IR (neat) 1661 cm$^{-1}$ (amide C=O str.)

EXAMPLE 9

Preparation of (N,N-diethyl)-(5S)-5-(N,N-dibenzylamino)-2-ethyl-4-oxo-hexanamide

To a solution of NaHMDS (0.52 mmol, 0.53 mL) in 1.0 mL THF at −78° C. was added a solution of α-(N,N-dibenzylamino)ethyl methyl ketone (0.5 mmol, 0.13 g) in 0.5 mL THF under argon atmosphere. After stirring the yellow colored solution for one hour, a solution of 2-bromo-(N,N-diethyl)-butyramide (0.51 mmol, 0.11 g) in 0.5 mL THF was added dropwise. The solution was stirred at −78° C. for 30 minutes and then at ambient temperature for another two hours before quenching with 2.0 mL of saturated solution of NH$_4$Cl. After a work-up as described in Example 8, the residue was purified by column chromatography over silica gel with 4:1 hexanes-ethyl acetate as the solvent system (Rf=0.21) to give 0.03 g of α-(N,N-dibenzylamino)ethyl methyl ketone, the starting ketone, and the product as a mixture of diastereomers (0.082 g, 55% yield based on recovered starting material) as a colorless oil. Analytical data: $^1$H NMR (very complex spectrum due to diastereomers, diastereotopic protons and rotamers due to rotation around the N—C=O bond); $^{13}$C NMR (one isolated diastereomer) 7.1, 11.7, 12.9, 14.4, 25.9, 37.6, 40.2, 41.9, 42.5, 54.6, 62.1, 127.1, 128.4, 128.6, 139.2 (C=O and N—C=O were not observed possibly due to the low concentration of the compound); IR (neat) 1720 (s, C=O str. for ketone), 1640 (s, C=O str. for amide) cm$^{-1}$. Mass spectrum (low resolution) 409 (M+1, 30%), 224 (M—MeCHNBn$_2$, 100%). HRMS for C$_{26}$H$_{37}$N$_2$O$_2$: 409.284 (calc'd 409.2846)

Examples 10 and 11 provide a detailed description for the preparation of (5S)-5-(N,N-dibenzylamino)-2-ethyl-4-oxo-hexanoic acid-tert-butyl ester from tert-butyl-2-bromobutyrate and α-(N,N-dibenzylamino)ethyl methyl ketone. This compound is reduced to the corresponding amino alcohol as described in detail above.

EXAMPLE 10

Preparation of tert-butyl-2-bromobutyrate tert-Butyl-2-bromobutyrate was synthesized according to the procedure described in Compagnone, R. S., and Rapoport, H. *J. Org. Chem.* 1986, 51, 1713.

EXAMPLE 11

Preparation of (5S)-5-(N,N-dibenzylamino)-2-ethyl-4-oxo-hexanoic acid-tert-butyl ester A solution of α-(N,N-dibenzylamino)ethyl methyl ketone (0.5 mmol, 0.13 g) in 0.5 mL THF was added to a solution of NaHMDS (0.53 mmol, 0.53 mL) in 1.0 mL THF at -78° C. under argon atmosphere. After stirring the yellow colored solution for one hour, a solution of tert-butyl-2-bromobutyrate (0.51 mmol, 0.11 g) in 0.5 mL THF was added dropwise. The solution was stirred at -78° C. for 30 minutes, and then at ambient temperature for another 2 hours, before quenching with 2.0 mL of saturated solution of NH$_4$Cl. After a work-up as described in Example 7, the residue was purified by column chromatography over silica gel with 4:1 hexanes-ethyl acetate as the solvent system (Rf=0.53) to give the product as a mixture of diastereomers (0.047 g, 23% yield) as a colorless oil. Analytical data: $^1$H NMR (300.15 MHz) δ 0.83 (t, J=7.5 Hz, 3H), 1.22–1.72 (m, 8H) 1.39 (s, 9H), 3.62–3.86 (m, 5H), 7.23–7.33 (m, 10H); Mass spectrum (low resolution) 410 (M+1, 30%), 224 (M—MeCHNBn$_2$, 100%). HRMS for C$_{26}$H$_{35}$O$_3$NLi: 416.2773 (calc'd 416–2768).

Examples 12 and 13 provide a detailed description for the preparation of methyl-(5S)-5-(N,N-dibenzylamino)-4-oxo-hexanoate from 1-bromo-(3S)-3-N,N-dibenzylamino-butan-2-one.

EXAMPLE 12

Preparation of 1-bromo-(3S)-3-N,N-dibenzylamino-butan-2-one

A solution of LDA was generated by addition of n-butyllithium (1.05 mmol, 2.5 M) to freshly distilled diisopropylamine (1.2 mmol, 0.16 mL) in 2.0 mL THF at -78° C. under argon atmosphere. To this solution was added a solution of α-S-(N,N-dibenzylamino)ethyl methyl ketone (1.0 mmol, 0.13 g) in 1.0 mL THF. The resulting solution was stirred at -78° C. for one hour and then a solution of bromine (1.05 mmol, 0.06 mL) in 0.5 mL CH$_2$Cl$_2$ was introduced dropwise. The reaction mixture was stirred at -78° C. for 10 minutes and then quenched with saturated solution of NaHCO$_3$. The organic layer was extracted with pentane (2×15.0 mL), washed with brine, dried over MgSO$_4$, and filtered. The solvent was removed in vacuo to obtain a yellow-orange colored oil which solidified on standing. The crude $^1$H NMR showed presence of starting material (approximately 5%), but the reaction product was used in the reaction described in Example 13 without further purification. Analytical data: $^1$H NMR (300.15 MHz) δ 1.21 (d, J=6.6 Hz, 3H), 3.60 (AB$_q$, δ$_A$=3.43, δ$_B$=3.69, J=13.5 Hz, 4H), 3.68 (q, J=6.6 Hz, 1H), 4.17 (AB$_q$, δ$_A$=4.14, δ$_B$=4.19, J=13.5 Hz, 2H), 7.23–7.37 (m, 10H).

EXAMPLE 13

Preparation of methyl-(5S)-5-(N,N-dibenzylamino)-4-oxo-hexanoate

Methyl acetate (1.0 mmol, 0.08 mL) was added dropwise to a solution of LDA (1.05 mmol) in 2.0 mL THF at -78° C., and the resulting solution was stirred for 45 minutes. Hexamethyl phosphoric triamide (1.0 mmol, 0.18 mL) was then added, and after 15 minutes a solution of α-(N,N-dibenzylamino)ethyl bromomethyl ketone (crude from the previous reaction, assumed to be 1.0 mmol) in 2.0 mL was added via syringe. The resulting solution was stirred at -78° C. for 45 minutes and then quenched with saturated solution of NaHCO$_3$. After a work-up as described in Example 8, 0.39 g of crude product was obtained. The product was further purified by column chromatography on silica gel with 8:1 hexanes-ethyl acetate as the solvent system (Rf= 0.33) to yield 0.21 g (62%) of methyl-(5S)-5-(N,N-dibenzylamino)-4-oxo-hexanoate as a colorless viscous oil. Analytical data: $^1$H NMR (300.15 MHz) δ 0.95 (d, J=6.6 Hz, 3H), 2.62–2.30 (m, 4H), 3.36 (q, J=6.2 Hz, 1H), 3.60 (AB$_q$, δ$_A$=3.41, δ$_B$=3.82, J=13.5 Hz, 4H), 3.49 (s, 3H), 7.23–7.37 (m, 10H); $^{13}$C NMR 5.1, 38.9, 48.8, 51.4, 54.4, 57.5, 126.9, 128.2, 128.8, 129.2, 139.4, 170.4, 208.2.

This invention has been described with reference to its preferred embodiments. Variations and modifications of the

We claim:

1. A compound of the formula:

wherein:
- $R^1$ is selected from the group consisting of the residue of an amino acid, peptide, alkyl, aryl, alkaryl, heteroaromatic, alkyl(heteroaromatic), arylamino and aralkyl groups;
- both $R^2$ moieties are benzyl or one $R^2$ moiety is benzyl and the other is selected from the group consisting of t-butyloxycarbonyl, benzyloxycarbonyl, and p-methoxybenzyl;
- $R^3$ is selected from the group consisting of alkyl, aryl, heteroaromatic, alkylheteroaromatic, aralkyl, and alkaryl;
- $R^4$ is selected from the group consisting of alkyl, alkaryl, aryl, aralkyl, heteroaromatic, and alkylheteroaromatic; and
- $R^5$ is selected from the group consisting of primary or secondary alkyl and benzyl.

2. A compound of the formula:

wherein:
- $R^1$ is selected from the group consisting of the residue of an amino acid, peptide, alkyl, aryl, alkaryl, heteroaromatic, alkyl(heteroaromatic), arylamino and aralkyl groups;
- $R^2$ is hydrogen, or both moieties are benzyl or one $R^2$ moiety is benzyl and the other is selected from the group consisting of t-butyloxycarbonyl, benzyloxycarbonyl, and p-methoxybenzyl;
- $R^3$ is selected from the group consisting of alkyl, aryl, heteroaromatic, alkylheteroaromatic, aralkyl, and alkaryl;
- $R^4$ is selected from the group consisting of alkyl, alkaryl, aryl, aralkyl, heteroaromatic, and alkylheteroaromatic; and
- $R^5$ is selected from the group consisting of primary or secondary alkyl and benzyl.

* * * * *